United States Patent [19]
Ostrander

[11] Patent Number: 5,513,642
[45] Date of Patent: May 7, 1996

[54] REFLECTANCE SENSOR SYSTEM

[75] Inventor: Lee E. Ostrander, Troy, N.Y.

[73] Assignee: Rensselaer Polytechnic Institute, Troy, N.Y.

[21] Appl. No.: 321,733

[22] Filed: Oct. 12, 1994

[51] Int. Cl.$^6$ ................................................ A61B 5/00
[52] U.S. Cl. ........................ 128/633; 128/664; 356/39
[58] Field of Search ................................ 128/633, 664, 128/665; 356/39, 40, 41

[56] References Cited

U.S. PATENT DOCUMENTS

| | | |
|---|---|---|
| 2,358,992 | 9/1944 | Millikan . |
| 4,223,680 | 9/1980 | Jobsis . |
| 4,321,930 | 3/1982 | Jobsis et al. . |
| 4,380,240 | 4/1983 | Jobsis et al. . |
| 4,510,938 | 4/1985 | Jobsis et al. . |
| 4,796,636 | 1/1989 | Branstetter et al. . |
| 5,057,695 | 10/1991 | Hirao et al. . |
| 5,218,962 | 6/1993 | Mannheimer et al. . |
| 5,419,321 | 5/1995 | Evans ..................................... 128/633 |

OTHER PUBLICATIONS

The Effects of Absorptive Layers on Light Reflectance, Muller and Ostrander, Published in Conference Proceedings, Oct, 28, 1993.
The Relationship of Surface Reflectance Measurements to Optical Properties of Layered Biological Media, Cui and Ostrander, Feb. 1992.
In Vivo Reflectance of Blood and Tissue as a Function of Light Wavelength, Cui, Ostrander, Lee, Jun. 1990.

Primary Examiner—Angela D. Sykes
Assistant Examiner—Eric F. Winakur
Attorney, Agent, or Firm—Notaro & Michalos

[57] ABSTRACT

A method for determining the content of chemical constituents in a biological tissue medium includes providing a probe comprising a light source and a plurality of photodetector strips circumferentially arranged around the light source. A wavelength for the illumination of the light source is selected and the photodetector strips are illuminated at the selected wavelength. Voltage readings are then taken for each photodetector strip. After taking the readings, the probe is placed on a surface of the tissue medium and the medium is illuminated at the selected wavelength. Voltage readings are again taken at each photodetector strip. The voltage readings taken from the tissue medium are then adjusted by dividing these readings by the initial voltage readings for each photodetector strip. A logarithm is taken for the adjusted voltage readings as a function of the separation distance between each photodetector strip and the light source. The values from the logarithmic function may be filtered according to a formula in which a smoothing approximation is utilized. A theoretical model is used to determine the flux of photons incident on each of the photodetector strips. Parameters are used to minimize the mean squared error or other error function when comparing the model values to the measured values.

5 Claims, 9 Drawing Sheets

RESPONSE OF THE PHOTODETECTOR

REFLECTANCE SENSOR SYSTEM

FIELD AND BACKGROUND OF THE INVENTION

The present invention relates, in general, to sensors, and in particular, to a new and useful light reflectance sensor system and method.

Reflectance sensor systems have been used for many purposes, including the determination of surface measurements for conditions related to blood perfusion at depths within layered biological tissue. Reflectance sensor systems usually consist of a physical sensor and an algorithm to determine diffusion constants and other derived quantities such as oxygenation of blood. Reflectance sensor systems sample the spatial or the temporal profile of photons from light, including infrared light, returning from a diffusive medium, such as biological tissue, following their injection into the medium. The rate of change, spatially or temporally, in the number of photons exiting the medium at some distance in space/time from the source are taken as being indicative of deeper layers of tissue.

Known reflector sensor systems have implemented the use of these physical principles by algorithms that compare reflectances at two or more sites or at two or more times following the injection of photons into the tissue medium. The data at larger separations or at longer times is then taken to be indicative of the diffusion constants K at depths where readings closer to the photon source are taken into account.

Alternatives to reflectance sensor systems, for the noninvasive measurement of reflectance in biological tissue at depth, and of comparable simplicity and ease of use, are not presently available. As a result, methods that provide shallow measurements are commonly used in the clinical environment. These alternative measurement methods include transcutaneous oxygen partial pressure, photoplethysmography, pulse oximetry and laser Doppler flowmetry.

Some of the known reflectance systems and methods as well as studies relating thereto are disclosed in Muller and Ostrander, "The Effects of Absorptive Layers On Light Reflectance", *Conference Proceedings*, Oct. 28, 1993; Cui and Ostrander, "The Relationship of Surface Reflectance Measurements to Optical Properties of Layered Biological Media", *IEEE Transactions on Biomedical Engineering*, Vol. 39, No. 2, February 1992; and Cui, Ostrander and Lee., "In Vivo Reflectance of Blood and Tissue as a Function of Light Wavelength", *IEEE Transactions on Biomedical Engineering*, Vol. 37, No. 6, June 1990.

Typical hardware used for the known reflectance sensor systems are disclosed in U.S. Pat. No. 4,510,938; 4,380,240; 4,321,930; and 4,223,680.

Further, U.S. Pat. No. 2,358,992 is relevant for its showing of an oxygen meter using colorimetry. U.S. Pat. No. 4,796,636 is relevant for disclosing a non-invasive reflective oximeter utilizing microprocessor based signal processing.

Also, see U.S. Pat. No. 5,057,695 which is relevant for showing a technique using a difference in light reception data from a single light source to a plurality of irradiation points, based on a difference in the length of the optical diffusion paths. Also, see U.S. Pat. No. 5,218,962 which is relevant for showing a multiple region pulse oximeter probe based on difference calculations of light passing through two regions of biological tissue.

Presently, however, there is no known reflectance sensor system which extracts data from monitored reflectances in an accurate and efficient manner.

SUMMARY OF THE INVENTION

The present invention is a system and method for measuring reflectance in a biological medium to determine the chemical constituents in the medium by utilizing a sensor to measure reflected photons within space slices or annular rings about a point of photon injection, and an algorithm to process the measurements to determine the diffusion constants. The sensor system of the present invention is an extension of previously known sensor designs. The algorithm of the present invention in combination with a sensor in the form of a circular probe system, is new.

Laboratory data acquired from muscle compartments in the human leg showed a measured reflectance profile that resembles the profile from a homogeneous diffusive medium over a selected range of source-detector separation. The algorithm of the present invention utilizes error minimization to achieve a best fit of the measured profile to the profile of a homogeneous diffusive medium. The best fit is described by two numbers from which the optical properties at depths are determined by empirical and/or theoretical relationships.

The diffusion constants K determined by the present invention allow for more accurate determination of conditions related to blood perfusion at depth within biological tissues such as muscle. By reducing measurement variability, the problem to be solved is to reduce the inaccuracy associated with the known methods, which are based upon a less accurate view of the relationship between reflectance profiles and optical properties at depth. Commercial advantages for the present invention exist since there is a demand for methods of noninvasively determining tissue parameters related to blood perfusion at depth within tissue.

The method and system according to the present invention includes providing a probe comprising a light source, such as high intensity light emitting diode (LED), and a plurality of photodetector strips which are circumferentially spaced around the LED. An illumination wavelength is then selected for the LED and the photodetector strips are illuminated by the LED at the selected wavelength. A test voltage reading is taken for each photodetector strip, after which the probe is placed on a surface of biological tissue medium for testing. The tissue medium is then illuminated at the selected wavelength and a voltage reading is taken for the tissue at each photodetector strip.

The tissue voltage reading for each detector strip is then adjusted by dividing the tissue voltage reading by the test voltage reading for each photodetector strip which was previously taken. The logarithms are then taken of the adjusted voltage readings as a function of the separation distance between each photodetector strip and the LED. The values determined from the logarithmic function may then be filtered according to a formula which includes a smoothing approximation.

On a theoretical basis, the flux of photons associated with each detector strip is determined according to a theoretical model in which values are assigned to parameters. When comparing the measured values versus the model results, the mean squared error between the model results and the measured values is minimized by selection of the parameters.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
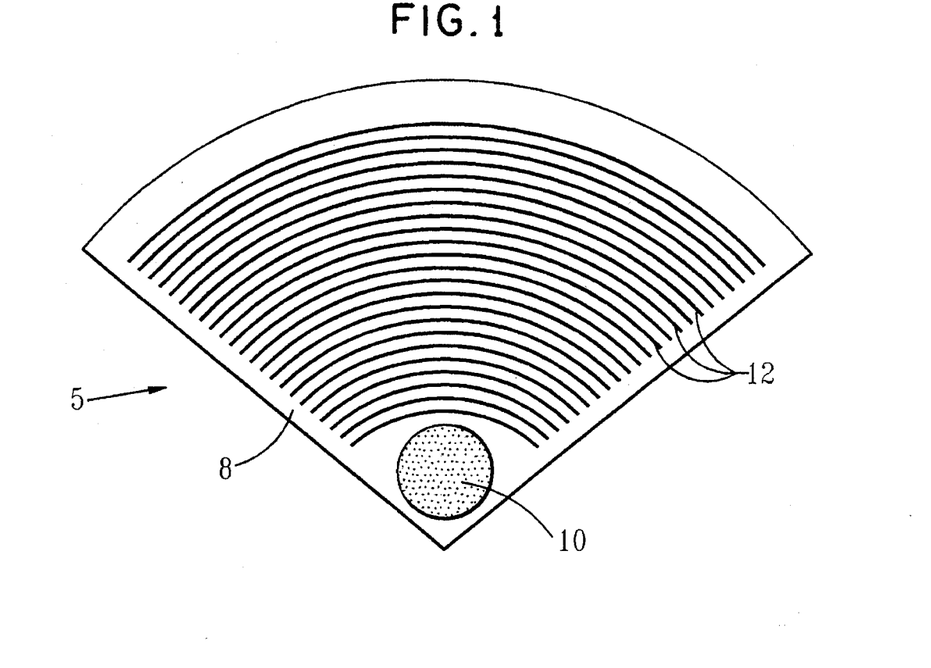
FIG. 1 is a schematic view of a reflectionance sensor system according to the present invention.
Figure 2:
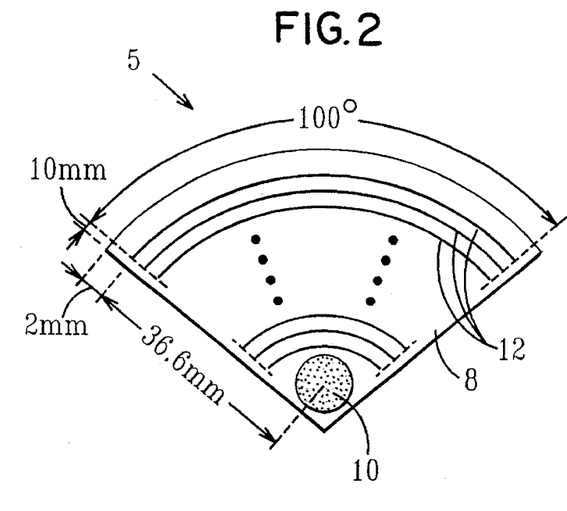
FIG. 2 is a schematic view of a reflectance sensor system arrangement distances.
Figure 2A:
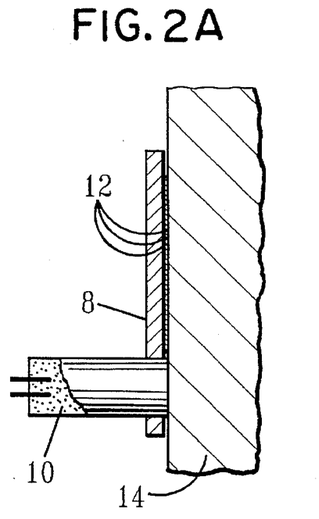
FIG. 2A is a schematic side view of the system of FIG. 1.

The present invention is a reflectance sensor method and system, which uses a probe, sensor or detector generally designated 5 in FIGS. 1, 2 and 2A, having a high-intensity light emitting diode (LED) 10 with an emitted light wavelength and using an average current of approximately 50 ma.

Figure 4:
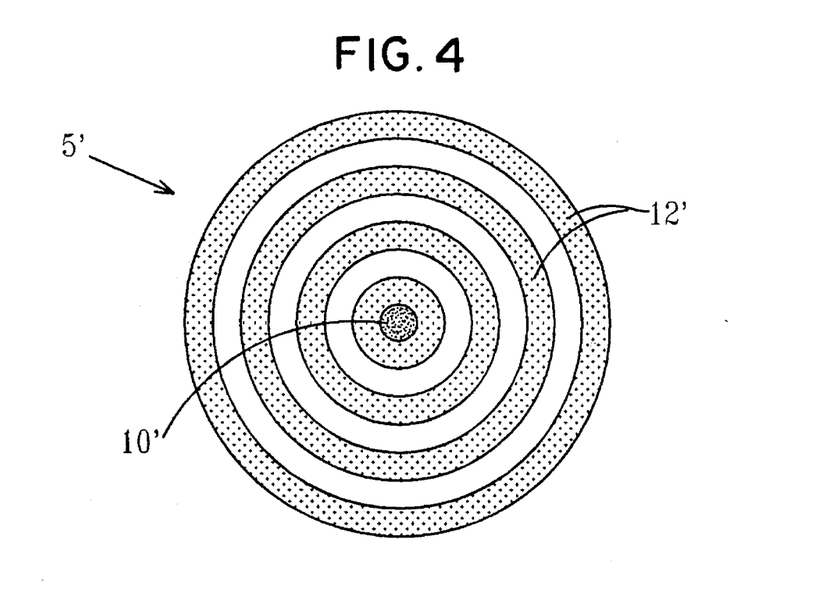
FIG. 4 is a schematic view of the reflectance sensor system of FIG. 1 in a circular arrangement.

A plurality of concentric photodetector strips 12 are arranged circumferentially around the LED 10 on an insulating substrate or support 8. Any number of photodetector strips 12 may be utilized and the arrangement 5 is not limited to any specific number of photodetectors 12, however, an arrangement having thirty-two photodetector strips has proven to be efficient. FIG. 4 illustrates a sensor system 5' having photodetector strips 12' arranged 360° around the LED or light source 10.

Figure 3:
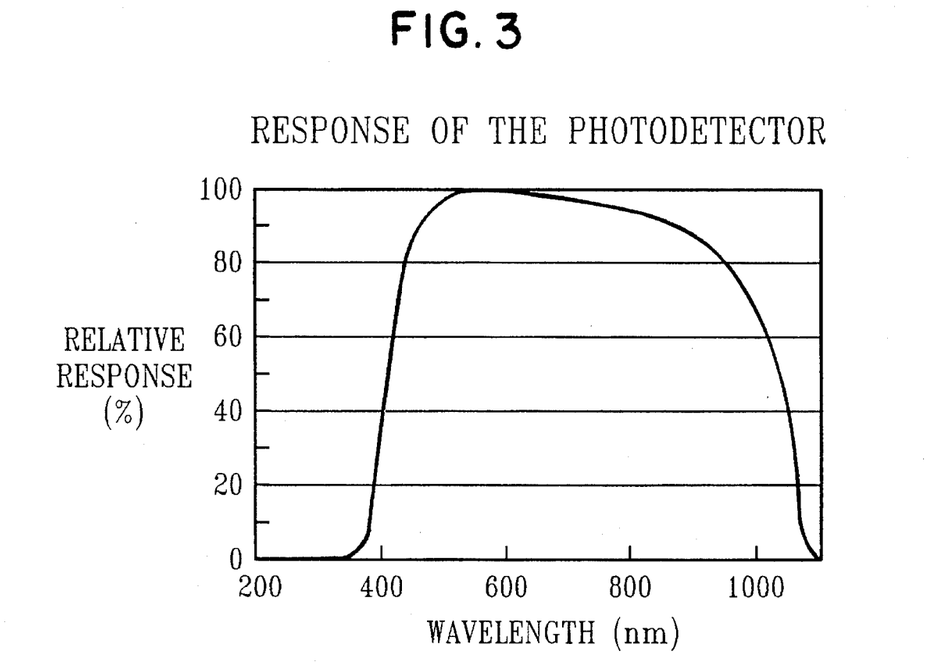
FIG. 3 is a graph plotting the relative response of a photo-detector for the system of FIG. 1, against wavelength.

Each of the photodetector strips 12 or 12' has an annular or segmental photo sensitive segment of approximately 0.9 mm width which is located at a fixed distance from the LED 10 or 10'. There is a spacing of approximately 0.1 mm between the photodetector strips 12. The illumination from the LED 10 is electrically modulated at approximately 2,000 Hz in order to attenuate inherent detector noise and the effect of stray light which requires amplitude demodulation of the signal received from the detector 5. A typical frequency (wavelength) response for the photodetector strips 12 or 12' is shown in FIG. 3.

Figure 5:
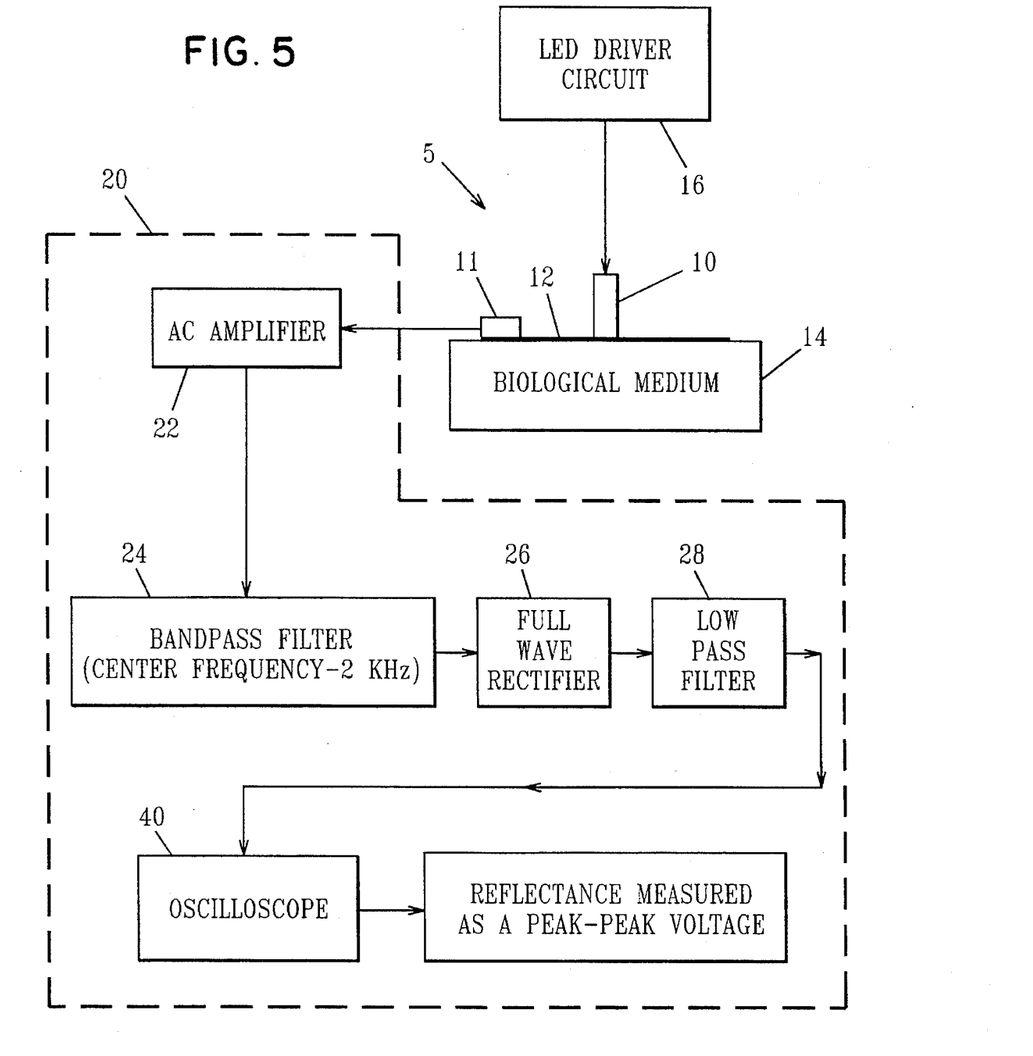
FIG. 5 is a schematic block diagram of a signal processing circuit for the sensor system of the present invention.
Figure 6:
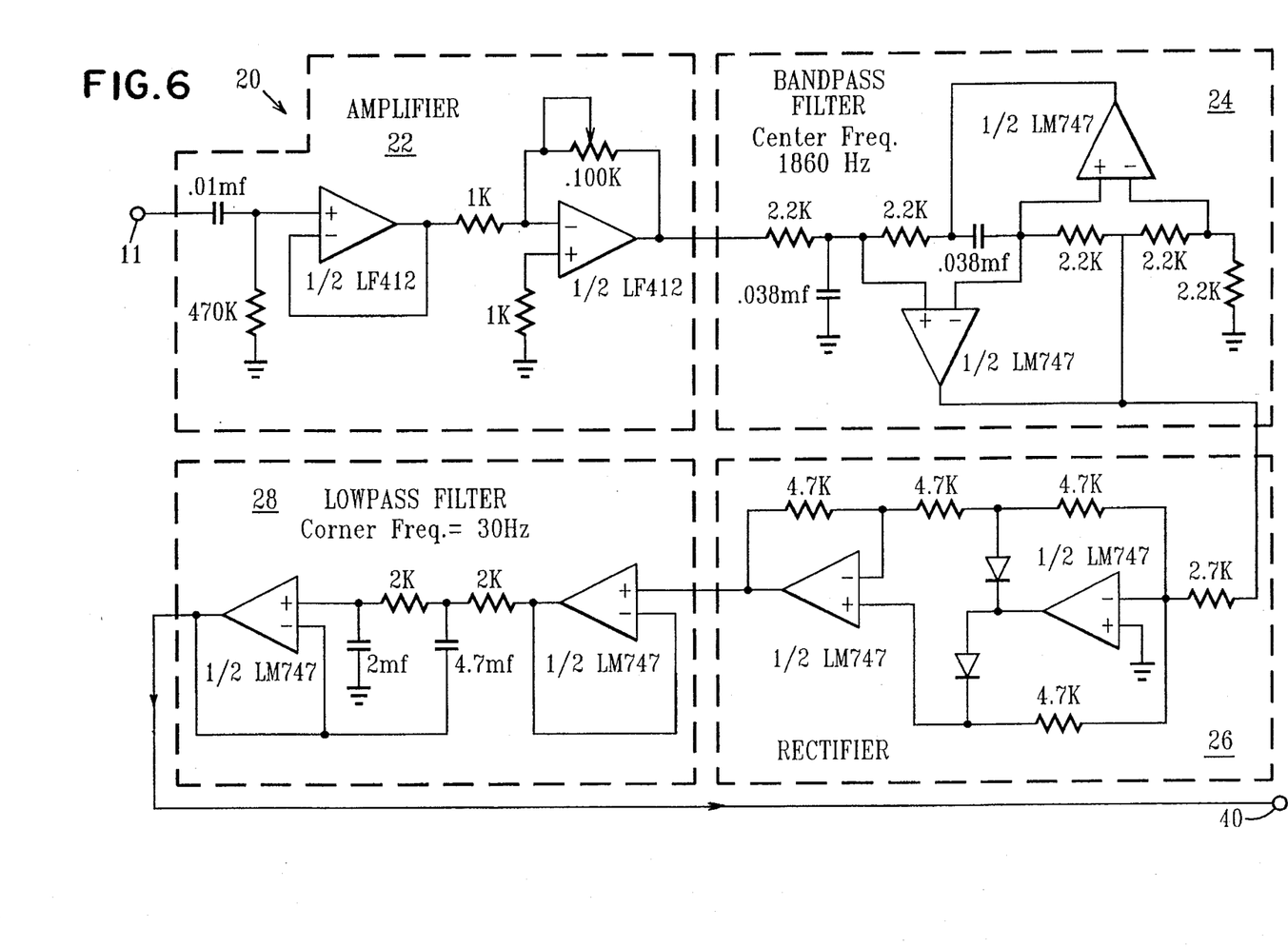
FIG. 6 is a schematic block diagram of a section of the circuit of FIG. 5.
Figure 7:
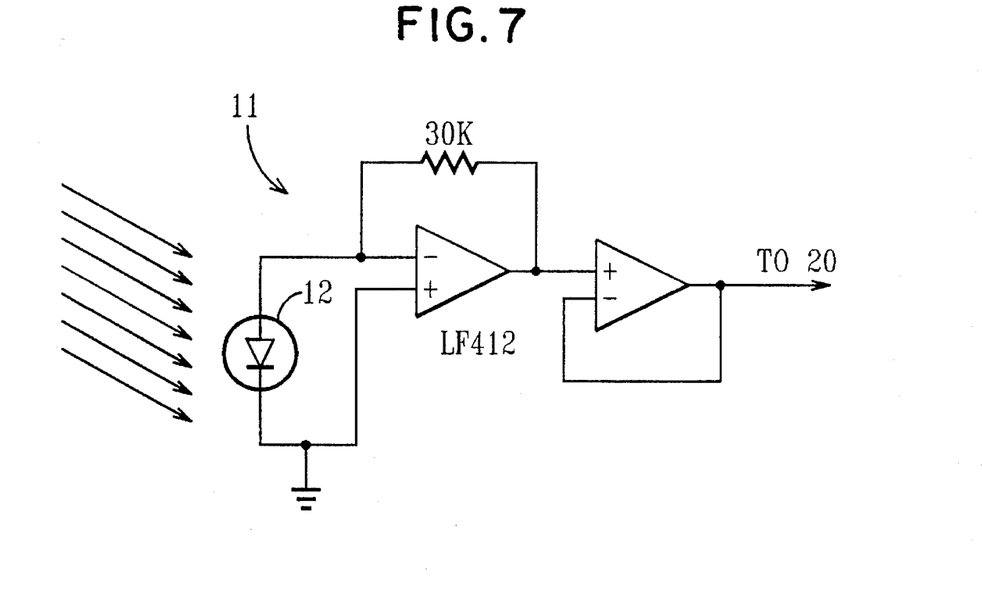
FIG. 7 is a schematic diagram of a photodetector preamplification circuit of the invention.
Figure 8:
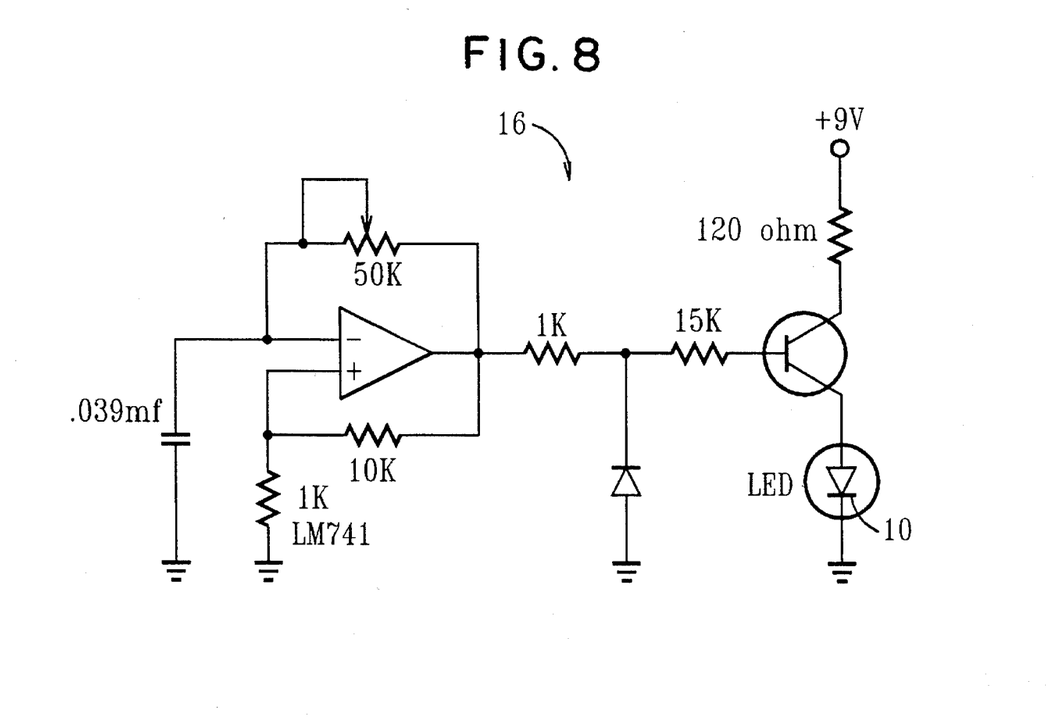
FIG. 8 is a schematic diagram of an LED driving circuit of the invention.

The sensor 5 utilizes an LED driver circuit 16 (FIG. 8) which generates and controls the emissions of the LED 10 as shown in FIG. 5. The LED 10 with circumferentially (either partly or wholly) arranged photo-detector strips 12 or 12' are placed on a biological tissue medium 14 for conducting reflectance testing. A photodetector pre-amplification circuit 11 (FIG. 7) is used to preamplify the signal prior to sending it to a reflectance sensor circuit 20 which is also illustrated in FIG. 6.

The reflectance sensor circuit 20 comprises an AC amplifier 22 which receives the signal from preamplification circuit 11 and amplifies the signal prior to sending the signal through band pass filter 24. After filtering, the signal is rectified by a full wave rectifier 26 and passed through a low pass filter 28 for further filtering. After filtering, the signal undergoes amplification at amplifier 32 prior to being displayed on an oscilloscope 40 for recording the signal. In order to calibrate the probe 5 or 5', the probe is first subjected to a uniform surface illumination at the selected wavelength. Voltage readings are taken from each of the photodetector strips 12 or 12'. The number of total readings are equivalent to the number of strips 12, i.e. thirty-two readings for thirty-two strips. These readings represent the sensitivities of the strips 12 and provide a means for calibrating the probe. Prior to taking data, the probe is placed on a reference diffusing medium and the intensity of the light emitting diode (LED) 10 or 10' is adjusted to achieve a preselected reference voltage at the first strip, so that the incident intensity of light into the medium is of known strength and is approximately equal in subsequent studies.

In use, the probe 5 or 5' is placed on the surface of the medium 14, such as skin, and voltage readings are taken from the output of the reflectance sensor circuit 40 at each of the strip positions. The separations of these strip positions from the LED ranges from 2.5 mm to 34.5 mm, although a larger range is possible and could be desirable in some scenarios. The readings are adjusted for differing sensitivities of the detectors by dividing the voltage readings by those obtained with the uniform illumination.

The adjusted readings are then used in the subsequent processing described below. First, the logarithm of the adjusted readings is obtained at each source-detector separation. Since the strips are narrow, i.e. a little less than 1 mm width, spatial noise occurs due to the variability of the material which is being measured. To help reduce the effects of this noise, the values are subjected to a boxcar filter, implemented by computer calculations. By designating S'(r) as the logarithm of the adjusted readings as a function of the source-detector separation r, then the filtered values S(r), are given by:

$$S(r_i) = \frac{1}{2N+1} \sum_{j=i-N}^{i+N} S'(r_j)$$

where $r_i$ is the distance from the source (10, 10') to detector i (12, 12'), and where N is chosen according to the amount of smoothing, i.e. an approximation with a higher degree of correspondence between spatially adjacent measurements. A value of N=3 was used in analysis, although any value for N is acceptable according to the desired amount of smoothing.

The resulting data are then compared with the photon diffusion theory for a homogeneous anisotropic diffusive medium and at radius r from the light source. The equation below shows the theoretically determined flux F(x) of photons incident on the detector placed at the surface of the medium. The purpose of the comparison is to obtain a parameterization of the biological medium data contained in the filtered readings {S(r)}. The equation providing the flux information is:

$$F(r) = (\alpha \cdot D) \cdot \frac{1}{r^2} \cdot \left(1 + \frac{1}{K \cdot r}\right) \cdot e^{-K \cdot r}$$

where K is the optical diffusion constant, ($\alpha \cdot D$) is a coefficient dependent upon scattering and absorption in the medium.

Figure 9:
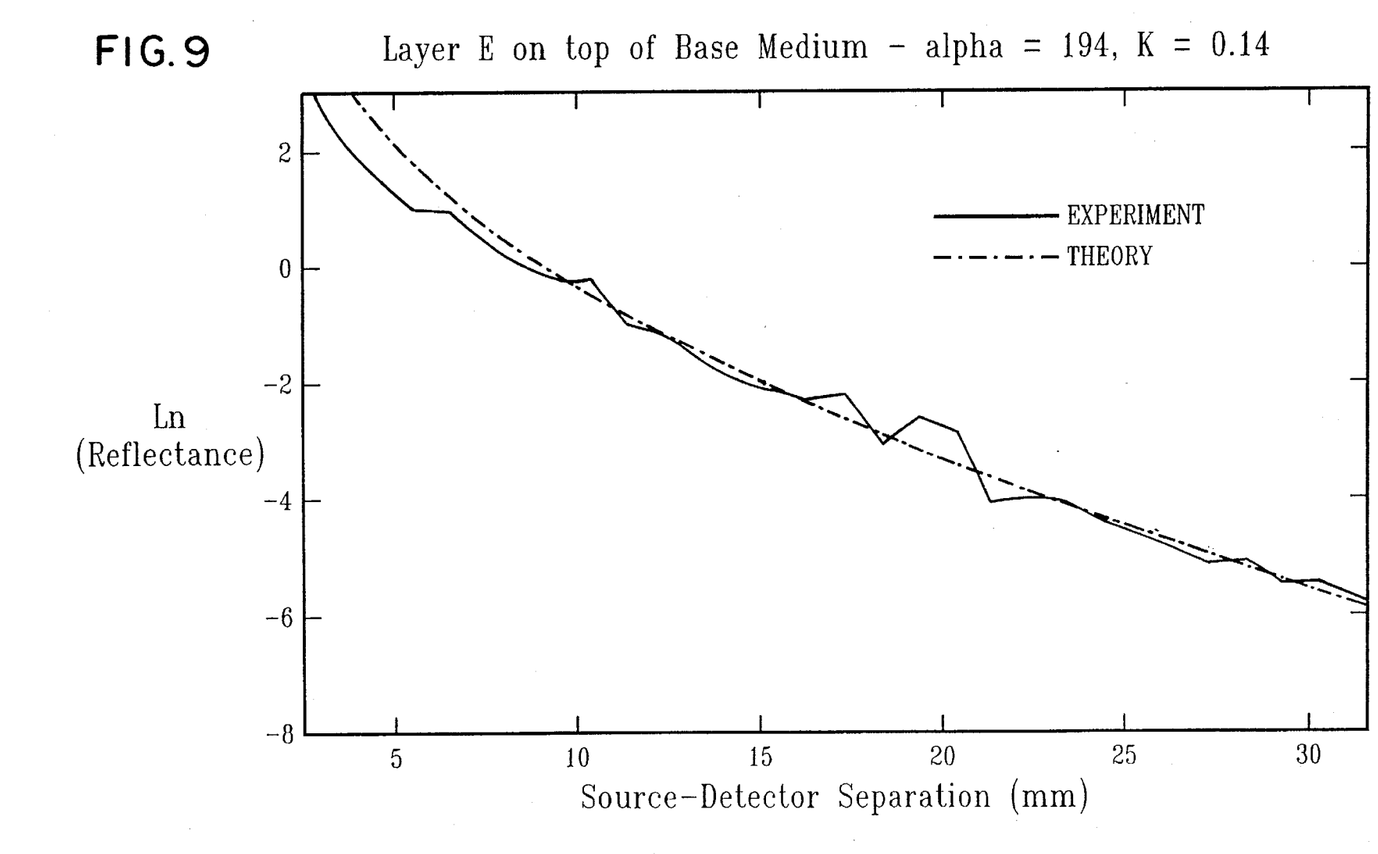
FIG. 9 is a graph comparing experimental data versus theoretical data having a first set of parameters.
Figure 11:
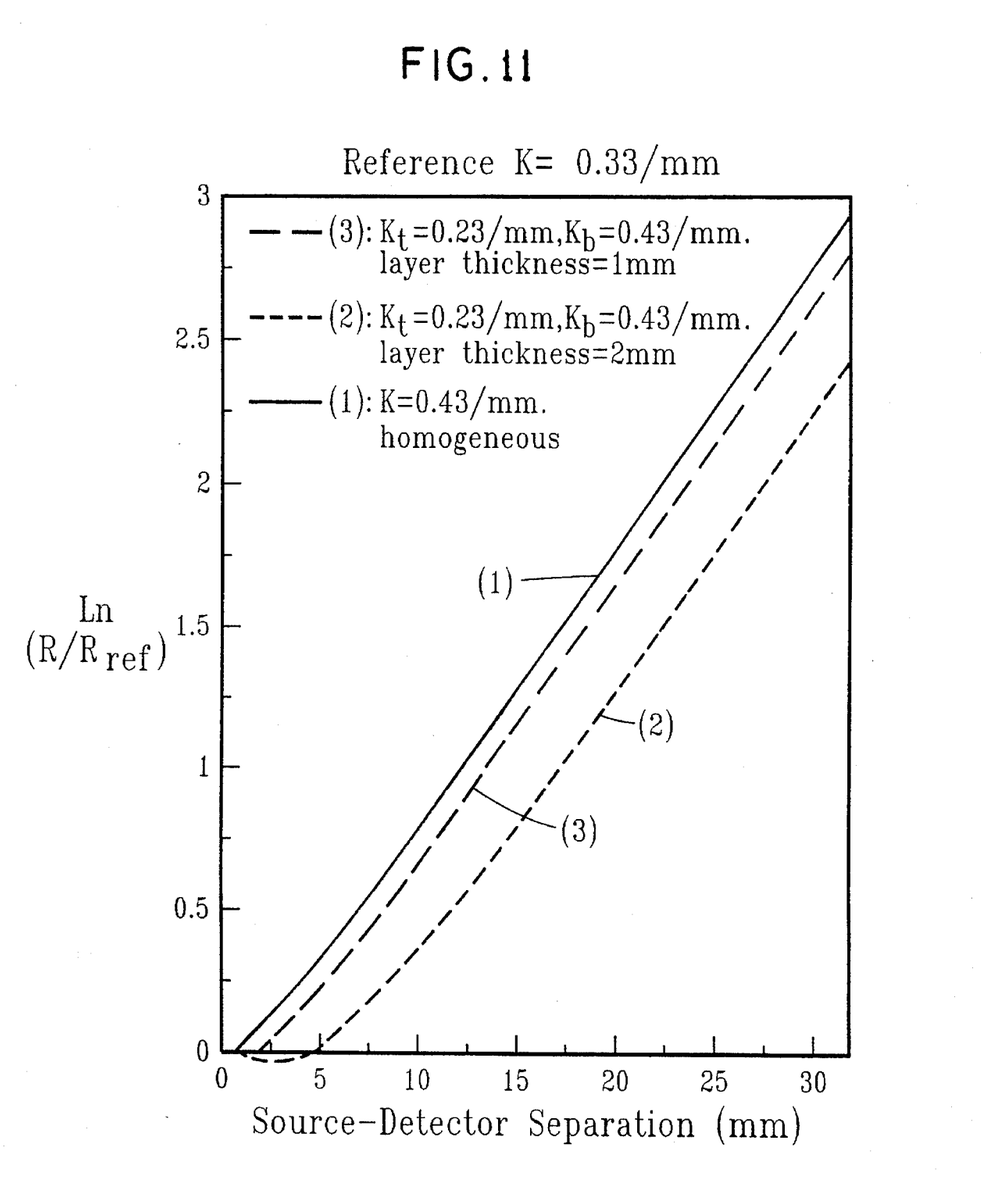
FIG. 11 is a graph plotting simulation results in which a layered medium tested with the system according to the present invention differs from a homogeneous reference medium.
Figure 12:
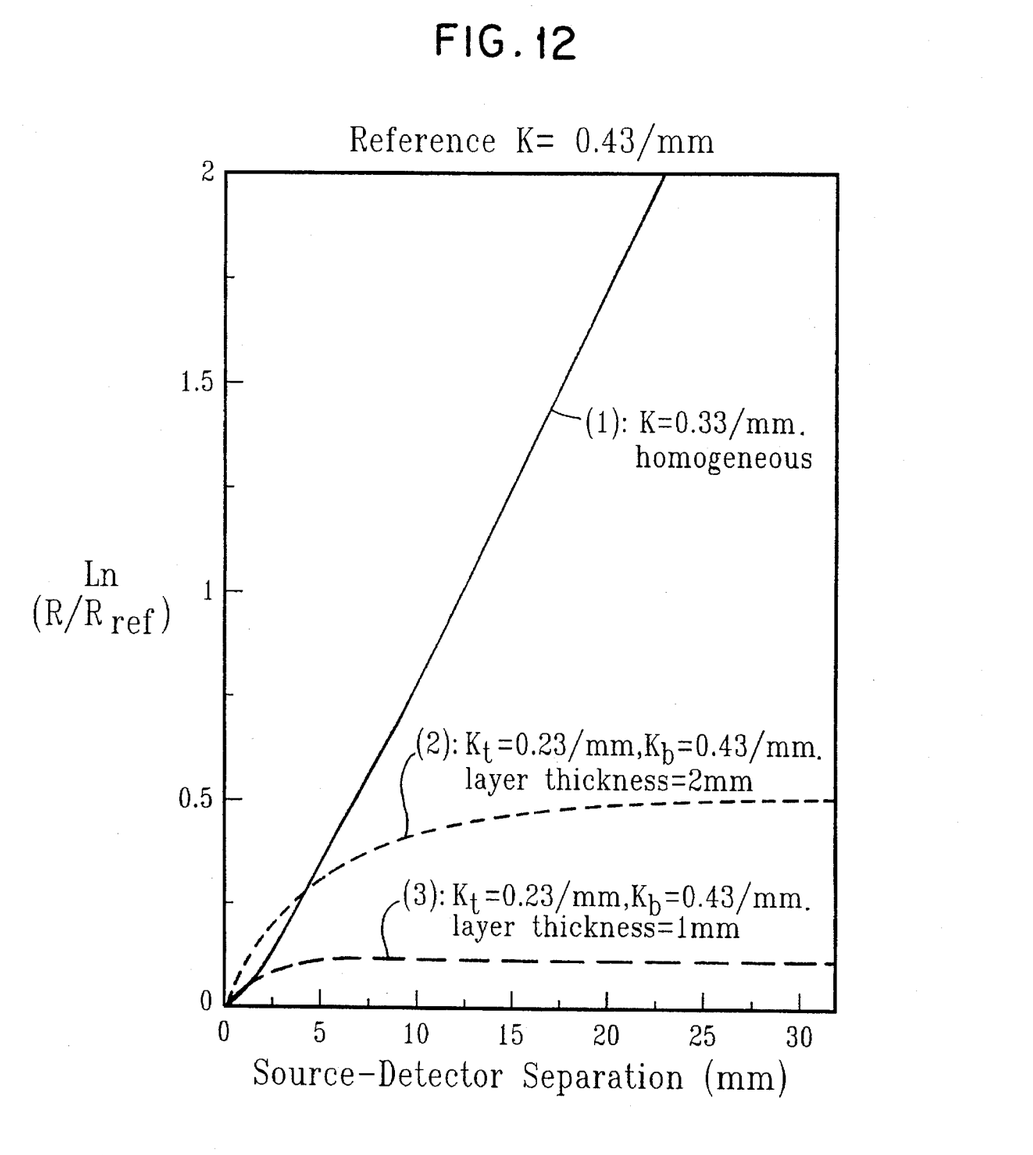
FIG. 12 is a graph plotting simulation results in which a layered medium tested with the system according to the present invention differs from a homogeneous reference medium and wherein the bottom layer of the tested medium has the same value for K as the homogeneous medium.

A program such as MATLAB (a trademark for a matrix-based program for scientific and engineering calculation by (The MathWorks, Inc.) produces values of parameters ($\alpha \cdot D$) and K which minimize the mean squared error between the theoretical model and the measured data after the aforementioned proceedings. Since the flux is nonlinear in K, the solution method is by iteration. Although faster methods may be possible, a Simplex search method can be used. Other error functions may be substituted for mean squared error. An example of a best choice of K, obtained by this process to match the theory and the experiment data, is shown in FIG. 9. FIGS. 11 and 12 illustrate values for K for various photodetector strip separation distances.

In FIGS. 11 and 12, the simulation results are shown in which the biological layered tissue medium differs from the homogeneous reference medium. The bottom layer of the biological medium in FIG. 12 has a diffusion constant $K_b$ which is the same as the reference K value for the homogeneous medium. In FIG. 11, the top layer and the bottom layer of the biological medium have values for K noted at $K_t$ and $K_b$, respectively which differ from the reference medium. The ordinate, $\pm \text{Ln}$ (R/R ref) is the natural log of R or reflectance for the medium, over R ref or a reference reflectance for a homogeneous medium.

Utilizing the sensor system described above, the present invention comprises a method in which the optical diffusion constant (K) is obtained. The constant K describes the travel of light through a homogeneous diffusive medium, illuminated with a beam of light having a small radius normal to or having a major normal component with respect to the surface of the medium. The constant K is an important intermediary for noninvasive devices that use light reflectance to determine the content of chemical constituents in tissue. The known methods prior to the present invention involved determining the slope of the curve from two points on the curve and approximating K by the inverse of the slope.

The method according to the present invention can be applied to many noninvasive devices. In particular, the present invention is applied to situations where the chemical constituent is oxygen bound to hemoglobin. Other applicable chemical constituents are bilirubin, glucose, myoglobin, fetal hemoglobin and melanin. Applications for the chemical information include determining the status of the patient's blood oxygenation in regional tissues, such as in limb and/or muscle tissues.

Figure 10:
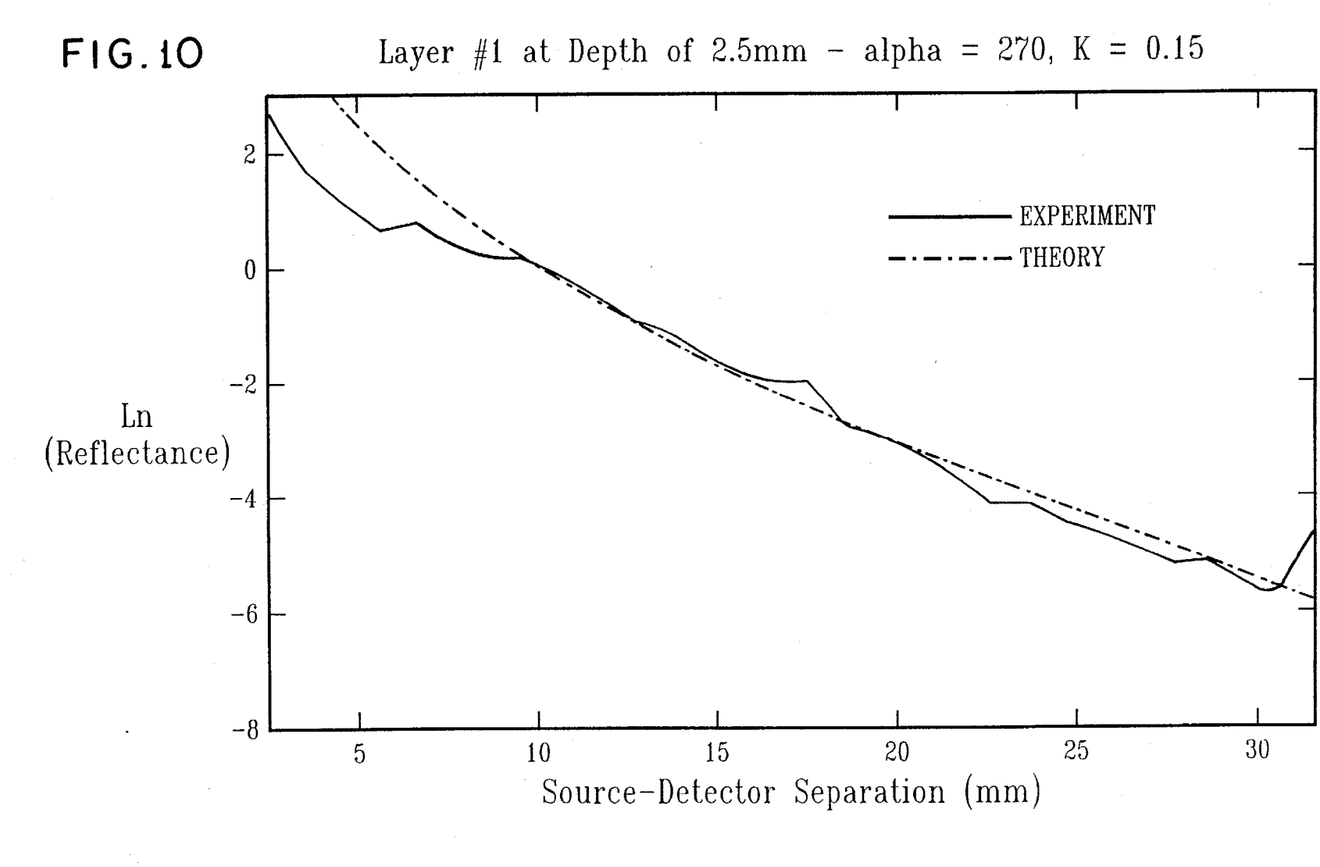
FIG. 10 is a graph comparing experimental data versus theoretical data for a second set of parameters.

The reflectance sensor system of the present invention can also be used when the data obtained is from tissue that is not homogeneous. The purpose in such a case is to find the equivalent homogeneous tissue representation. Where the tissues near the light source differ from tissues at greater distances, the reflectance at closer distances may be ignored in the fitting process. This is shown in FIG. 10 where data for the experiment does not match the homogeneous model at closer distances. The method may be applied over a range of distances, while ignoring closer or further distances.

While a specific embodiment of the invention has been shown and described in detail to illustrate the application of the principles of the invention, it will be understood that the invention may be embodied otherwise without departing from such principles.

What is claimed is:

1. A method for determining the content of chemical constituents in a medium through light reflectance comprising the steps of:

providing a probe comprising a light source and a plurality of photodetector strips circumferentially spaced around the light source and at different separation distances between the light source and each photodetector strip;

selecting a wavelength for illumination of the photodetector strips;

uniformly illuminating the photodetector strips at the selected wavelength;

taking a test voltage reading from each photodetector strip;

placing the probe on a surface of the medium;

illuminating the medium at the selected wavelength using the light source;

taking a voltage reading from each photodetector strip;

adjusting the voltage reading from each photodetector strip by dividing the voltage reading by the test voltage reading from each photodetector strip;

taking the logarithm of the adjusted voltage reading where S'(r) is the logarithm of the adjusted voltage reading as a function of the separation distance r between each photodetector strip and the light source;

filtering values from the logarithmic function according to the formula:

$$S(r_i) = \frac{1}{2N+1} \sum_{j=i-N}^{i+N} S'(r_j)$$

where S(r) are the filtered values, $r_i$ is the distance from the light source to a photodetector strip i and N is a value based on a smoothing approximation, including N= zero; and using the filtered values as an indication of the content of chemical constituents in the medium.

2. The method according to claim 1, including theoretically determining a flux of photons reflected from the medium and incident on the photodetector strips according to the model:

$$F(r) = \alpha \cdot D \cdot \frac{1}{r^2} \cdot \left(1 + \frac{1}{K \cdot r}\right) \cdot e^{-K \cdot R}$$

where F(r) equals the flux, and ($\alpha \cdot D$) and K are values of parameters to minimize an error between the model and the filtered values.

3. The method according to claim 2, including comparing the filtered values to the model results.

4. The method according to claim 1, including providing the photodetector strips to be separated from the light source at a distance ranging from 2.5 to 34.5 mm.

5. The method according to claim 1, including providing the light source to be a light emitting diode (LED).

\* \* \* \* \*